United States Patent [19]

DesJardin et al.

[11] Patent Number: 4,785,112

[45] Date of Patent: Nov. 15, 1988

[54] PROCESS FOR THE PRODUCTION OF 2,3,5,6-TETRACHLOROPYRIDINE AND 2,3,6-TRICHLOROPYRIDINE

[75] Inventors: Michael A. DesJardin, San Ramon; Todd E. Kindorf, Orinda, both of Calif.

[73] Assignee: The Dow Chemical Company, Midland, Mich.

[21] Appl. No.: 145,799

[22] Filed: Jan. 19, 1988

Related U.S. Application Data

[63] Continuation-in-part of Ser. No. 50,186, May 13, 1987, abandoned.

[51] Int. Cl.$^4$ .............................................. C07D 213/04
[52] U.S. Cl. .................................................. 546/345
[58] Field of Search ........................................ 546/345

[56] References Cited

U.S. PATENT DOCUMENTS

| | | | |
|---|---|---|---|
| 3,251,848 | 5/1966 | Taplin | 546/345 |
| 3,370,062 | 2/1968 | Corran | 546/345 |
| 3,420,833 | 1/1969 | Taplin | 546/345 |
| 3,538,100 | 11/1970 | Smith | 546/345 |
| 4,281,135 | 7/1987 | Perettie et al. | 546/345 |

OTHER PUBLICATIONS

H. Suschitsky (Editor), *Polychloroaromatic Compounds*, Plenum Press, London, 1974, pp. 225–227 and 439–440.
Derwent Abstract of EP 239,964, 10/7/87.
Derwent Abstract of EP 239,905, 10/7/87.

*Primary Examiner*—Richard A. Schwartz
*Attorney, Agent, or Firm*—D. Wendell Osborne

[57] ABSTRACT

Vapor phase chlorination of 2,6-dichloropyridine produces 2,3,6-trichloropyridine selectively over isomeric 2,4,6-trichloropyridine and of 2,3,6-trichloropyridine produces 2,3,5,6-tetrachloropyrindine in high selectivity over isomeric 2,3,4,6-tetrachloropyridine at temperatures of 300° C. to 450° C. The products are intermediates for insecticides and herbicides.

9 Claims, No Drawings

PROCESS FOR THE PRODUCTION OF 2,3,5,6-TETRACHLOROPYRIDINE AND 2,3,6-TRICHLOROPYRIDINE

CROSS-REFERENCE TO RELATED APPLICATION

This application is a continuation-in-part of application Ser. No. 050,186, filed May 13, 1987, now abandoned.

BACKGROUND OF THE INVENTION 2,3,5,6-Tetrachloropyridine and 2,3,5-trichloropyridine are chemical intermediates which are extensively used in the production of commercial insecticides and herbicides. Their production has been the object of many investigations and new methods having improved economics or other desirable features continue to be sought. Methods which employ available starting materials of much lower value or which might otherwise be disposed of as waste are particularly valuable. The present invention relates to such a method.

The vapor phase chlorination of pyridine to obtain various mono- and polychloropyridine products is known. In one study, the intermediate mono- and polychloropyridine compounds were identified and the rate constants for each chlorination event at 500° C. were determined (H. Suschitzky, *Polychloroaromatic Compounds* (1974), page 440). Analysis of the rate constants given leads to the conclusion that under these conditions 2,3,6-trichloropyridine will produce 2,3,5,6- and 2,3,4,6-tetrachloropyridines in an approximately 3 to 1 ratio and 2,6-dichloropyridine will produce 2,3,6- and 2,4,6-trichloropyridines in an approximately 1 to 3 ratio.

SUMMARY OF THE INVENTION

It has now been found that 2,3,5,6-tetrachloropyridine and 2,3,6-trichloropyridine can be produced with high selectivity by the vapor phase chlorination respectively of 2,3,6-trichloropyridine and 2,6-dichloropyridine. 2,3,5,6-Tetrachloropyridine can likewise be produced from 2,6-dichloropyridine. Ratios of 2,3,5,6- to 2,3,4,6-tetrachloropyridine of at least 8:1 and usually greater than 10:1 are obtained from 2,3,6-trichloropyridine and ratios of 2,3,6- to 2,4,6-trichloropyridine of at least 0.7:1 and usually greater than 1:1 are obtained from 2,6-dichloropyridine by chlorination under the conditions of the present invention.

In the present invention a polychloropyridine of the formula

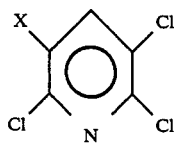

wherein X represents Cl or H is selectively prepared by a process which comprises contacting with chlorine in the vapor phase at about 300° C. to about 450° C. a less chlorinated polychloropyridine of the formula

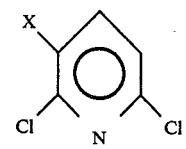

wherein X represents Cl or H. No catalyst or porous material such as silica or carbon is required. The polychloropyridine products prepared in the process are readily recoverable by condensation of the reaction mixtures and are readily purified by distillation or crystallization.

Surprisingly high yields of 2,3,5,6-tetrachloropyridine and 2,3,6-trichloropyridine are obtainable by the process due to the unexpectedly high selectivity of the chlorination under the specified conditions.

DETAILED DESCRIPTION OF THE INVENTION 2,3,5,6-Tetrachloropyridine is produced in high yield and with excellent selectivity in the process of the present invention by chlorination of 2,6-dichloropyridine, 2,3,6-trichloropyridine or mixtures of the two in the vapor phase under specified conditions. In a like manner, 2,3,6-trichloropyridine is produced in good yield and with excellent selectivity from 2,6-dichloropyridine.

Chlorine and the polychloropyridine reactant are combined and allowed to react in the vapor phase. Any reactor which is suitable for vapor phase chlorination reactions can be used in the process. Such reactors may be designed for either batch or continuous operations; however, those designed for continuous operation are preferred. Additionally, the reactor may be designed for plug flow, turbulent flow, transition flow or other types of flow and may involve plain, baffled or packed cavities. Generally, such reactors are constructed so that there is efficient mixing of chlorine and the compound to be chlorinated. This is variously accomplished by means of inlet patterns, turbulent flow, reactor packing, and the like. One type of reactor suitable for the process and its operation are described in U.S. Pat. No. 3,420,833. Similar reactors modified to alter performance, such as by the addition in the vicinity of the reactor outlet of secondary means for injecting diluents into the reactor, in order to improve the uniformity and control of the temperature within the reactor when the reactor is used for exothermic processes like those of the present invention, are often advantageously employed.

Sufficient chlorine is employed in the process to effect the desired chlorination and to provide a suitable reaction rate, but not so much as to create a chlorine recycle problem. The molar ratio of chlorine to polychloropyridine reactant employed generally ranges from abut 2:1 to about 40:1. Preferably, ratios of about 3:1 to about 30:1 and more preferably, ratios of at least 6:1 to about 30:1 are employed.

An inert diluent is normally employed in the process as an aid to mixing and to promote temperature and flow rate control. Chlorocarbons which are unreactive in the process, such as carbon tetrachloride and tetrachloroethylene, and unreactive gases, such as nitrogen and argon, are typical examples. Carbon tetrachloride and nitrogen, used separately or together, are often preferred. The means of introducing the inert diluent into the reactor is not critical, but it is often preferred to introduce it as a mixture with the polychloropyridine reactant.

The weight ratio of diluent to polychloropyridine reactant is typically about 20:1 to about 0.5:1. The present process gives 2,3,6-trichloropyridine or 2,3,5,6-tetrachloropyridine in high selectivity and good yield when the reactor is maintained at about 300° C. to about 450° C. Above this temperature, the selectivity of the reaction to 2,3,6-trichloropyridine and 2,3,5,6-tetrachloropyridine decreases and over-chlorination to pentachloropyridine takes place. As a result, the yields of the desired products are reduced. At lower temperatures, the process is too slow to be commercially useful. Reaction temperatures above about 320° C. are preferred and those above about 350° C. are especially preferred. Reaction temperatures below about 450° C. are preferred as are those below 440°, 430°, and 420° C.

The pressure in the reactor is not critical. Pressures from atmospheric to about 200 psi are typical and from atmospheric to about 100 psi are preferred. Typically, the reactor pressure is simply that which normally develops in the reactor under the conditions employed although the reaction rate is faster at higher pressures and higher pressures may, therefore, be preferred.

The chlorination reaction mixture is retained in the reactor until a significant portion of the 2,6-dichloropyridine or 2,3,6-trichloropyridine reactant has been consumed or until a significant amount of 2,3,6-trichlorpyridine or 2,3,5,6-tetrachloropyridine product has formed. Reaction times (retention times in continuous reactors) of about 0.1 sec. to about 180 sec. are typical while times of about 1 sec. to about 120 sec. are preferred. Reaction times are generally controlled by the size and shape of the reactor and the ratios and flow rates of the reactants and diluents employed.

At the conclusion of the reaction period, the reaction mixtures obtained are usually cooled to condense the organic constituents and, optionally, the hydrogen chloride by-product. This is typically accomplished by passing the vapors through a quantity of cooled organic solvent, such as carbon tetrachloride or methylene chloride. Carbon tetrachloride is preferred. It is often convenient to employ a quantity of previously obtained reaction product for this purpose. Typically, the organic components of the mixture are condensed and the major portion of the hydrogen chloride by-product is allowed to exit the system as a gas. Condensation of the reaction products by external cooling is also a suitable method.

The 2,3,6-trichloropyridine and 2,3,5,6-tetrachloropyridine prepared in the process are separable from the condensate described above by conventional means. Typically, the condensate is distilled using one or more distillation apparatuses. Unreacted starting materials and intermediates are lower boiling than the desired products and can be readily separated and recovered by distillation. They can be recycled to the chlorination reactor to improve the efficiency of the process. Over-chlorination by-products are higher boiling and can also be readily separated by distillation. Isomers can be removed by careful fractional distillation, by crystal refining, by recrystallization from appropriate organic solvents, or by other conventional means.

2,6-Dichloropyridine and 2,3,6-trichloropyridine are available compounds which can be prepared by the chlorination of pyridines and picolines and by other methods well known in the art. They are often obtained as unwanted co-products in pyridine and picoline chlorination processes.

The following examples are presented to illustrate the process. They should not be construed as limiting the claims.

EXAMPLE 1

An isothermal plug flow reactor constructed of Nickel-200 and consisting of four 4 ft. sections of 0.62 in. I.D. (0.75 in. O.D.) pipe enclosed inside a furnace and heated by four semi-cylindrical Lindberg heaters regulated by a Diogenes controller was employed. The reactor was equipped with a 1 ft. Nickel-200 Kenics static mixer at the inlet end. A 0.5 in. O.D. nitrogen feed pipe and a 0.5 in. O.D. double shell Nickel-200 chlorine/nitrogen feed pipe (chlorine in the inner shell and nitrogen in the outer shell), both of which were surrounded by four semi-cylindrical Lindberg heaters and equipped with rotameters were used to transport the reactants to the mixer. A polychloropyridine evaporation chamber with an inlet port for the polychloropyridine was installed in the nitrogen feed pipe between the heaters and the mixer. The reactor was further equipped on the outlet end with a cold-trap assembly consisting of two or three traps containing a dry ice-methylene chloride slurry and a carbon tetrachloride quench column.

2,3,6-Trichloropyridine was dissolved in carbon tetrachloride to obtain a ten percent solution and this was fed to the reactor operating under the conditions shown in the table below. The total contents of the traps and quench column were allowed to evaporate to remove the highly volatile components and were then analyzed by internal standardized capillary gas chromatography. The results are shown in the following table.

| | | | | EFFLUENT ANALYSIS (Mole Percent) | | | | |
|---|---|---|---|---|---|---|---|---|
| Run No. | Temp., °C. | Res. Time, Sec. | $Cl_2$:SM* molar ratio | 2,3,6-tri-chloro-pyridine | 2,3,5,6-tetra-chloro-pyridine | 2,3,4,6-tetra-chloro-pyridine | 2,3,5,6:2,3,4,6 ratio | Penta-chloro-pyridine |
| 1 | 440 | 0.49 | 16.3 | 87.5 | 11.9 | 0.5 | 24 | 0.08 |
| 2 | 440 | 0.49 | 16.9 | 83.5 | 16.1 | 0.4 | 40 | 0.01 |
| 3 | 410 | 0.49 | 18.0 | 89.0 | 11.0 | **ND | >100 | ND |
| 4 | 410 | 0.49 | 18.8 | 84.3 | 15.7 | ND | >157 | ND |
| 5 | 380 | 0.49 | 20.7 | 86.4 | 13.6 | ND | >136 | ND |
| 6 | 380 | 0.50 | 22.8 | 86.3 | 13.7 | ND | >137 | ND |
| 7 | 350 | 0.51 | 25.5 | 87.6 | 12.4 | ND | >124 | ND |
| 8 | 350 | 0.50 | 21.2 | 94.1 | 5.9 | ND | >59 | ND |
| 9 | 320 | 0.50 | 20.0 | 95.8 | 4.2 | ND | >42 | ND |
| 10 | 320 | 0.50 | 20.4 | 95.2 | 4.8 | ND | >48 | ND |

*SM is "starting material" - 2,3,6-trichloropyridine
**ND is "not detected"; lower limit of detection below about 0.10 percent

EXAMPLE 2

The reactor and procedure described in Example 1 were employed. Chlorine and 2,6-dichloropyridine (as a ten percent solution in carbon tetrachloride) were fed to the reactor in a 20:1 mole ratio along with an appropriate amount of nitrogen to achieve the desired residence times. The conditions employed and results obtained are given in the following table.

| | | | EFFLUENT ANALYSIS (Mole Percent) | | | | | | |
|---|---|---|---|---|---|---|---|---|---|
| Run No. | Temp., °C. | Res. Time, Sec. | 2,6-dichloro-pyridine | 2,4,6-tri-chloro-pyridine | 2,3,6-tri-chloro-pyridine | 2,3,6: 2,4,6 ratio | 2,3,4,6-tetra-chloro-pyridine | 2,3,5,6-tetra-chloro-pyridine | 2,3,5,6: 2,3,4,6 ratio |
| 1 | 450 | 0.69 | 91.33 | 4.74 | 3.52 | 0.74 | *ND | 0.41 | >4 |
| 2 | 450 | 0.69 | 90.43 | 5.12 | 3.86 | 0.75 | 0.06 | 0.53 | 9 |
| 3 | 430 | 0.69 | 94.81 | 2.40 | 2.31 | 0.96 | ND | 0.48 | >5 |
| 4 | 430 | 0.69 | 95.10 | 2.34 | 2.16 | 0.92 | ND | 0.40 | >4 |
| 5 | 410 | 0.70 | 97.02 | 1.03 | 1.60 | 1.55 | ND | 0.36 | >4 |
| 6 | 410 | 0.69 | 96.37 | 1.09 | 2.15 | 1.97 | ND | 0.39 | >4 |
| 7 | 380 | 1.69 | 97.17 | 0.79 | 1.55 | 1.96 | ND | 0.49 | >5 |
| 8 | 380 | 1.71 | 97.21 | 0.88 | 1.43 | 1.63 | ND | 0.48 | >5 |

*ND is "not detected"; limit of detection below about 0.10 percent

EXAMPLE 3

A simple 5.8L quartz 5/1 (length to diameter) vapor phase chlorinator equipped with electrical heaters, a temperature controller, chlorine and polychloropyridine inlet tubes, and, on the outlet end, two ice-water cooled cold traps and a scrubber column connected in series was employed. The chlorine and polychloropyridine inlet tubes were further equipped with heaters. 2,3,6-Trichloropyridine as a 10 percent solution in carbon tetrachloride was vaporized and fed into the reactor and chlorine was fed from a cylinder using a rotameter to control the rate. At the temperature setting of 350° C. (the actual temperature in the reactor ranged from about 320° C. at the inlet to about 380° C. at the outlet) with a residence time of 23.5 sec. and a mole ratio of chlorine to 2,3,6-trichloropyridine of 20, the effluent analyzed (mole percent) as follows: starting material, 95.74 percent; 2,3,4,6-tetrachloropyridine, 0.18 percent; 2,3,5,6-tetrachloropyridine, 1.70 percent; and pentachloropyridine, 2.27 percent. The ratio of 2,3,5,6-tetrachloropyridine to 2,3,4,6-tetrachloropyridine was, accordingly, 9.4.

What is claimed is:

1. A process for selectively preparing a polychloropyridine of the formula

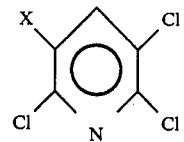

wherein X represents Cl or H which comprises contacting with chlorine in the vapor phase at about 300° C. to about 450° C. a less chlorinated polychloropyridine of the formula

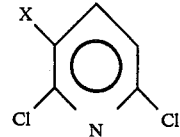

wherein X represents Cl or H.

2. A process according to claim 1 wherein the contacting is done at about 320° C. to about 450° C.

3. A process according to claim 1 wherein the contacting is conducted in a continuous manner.

4. A process according to claim 3 wherein the contacting is conducted under conditions of turbulent or transition flow.

5. A process according to claim 1 wherein the polychloropyridine prepared is further recovered by condensation.

6. A process according to claim 5 wherein the polychloropyridine recovered is further purified by distillation.

7. A process according to claim 1 wherein 2,6-dichloropyridine is contacted with chlorine and 2,3,6-trichloropyridine is prepared.

8. A process according to claim 1 wherein 2,6-dichloropyridine is contacted with chlorine and 2,3,5,6-tetrachloropyridine is prepared.

9. A process according to claim 1 wherein 2,3,6-trichloropyridine is contacted with chlorine and 2,3,5,6-tetrachloropyridine is prepared.

* * * * *